(12) United States Patent
Matsutani

(10) Patent No.: US 7,789,730 B2
(45) Date of Patent: Sep. 7, 2010

(54) METHOD OF MANUFACTURING TREATMENT DEVICE AND TREATMENT DEVICE

(75) Inventor: Kanji Matsutani, Utsunomiya (JP)

(73) Assignee: MANI, Inc., Utsunomiya-shi (JP)

( * ) Notice: Subject to any disclaimer, the term of this patent is extended or adjusted under 35 U.S.C. 154(b) by 66 days.

(21) Appl. No.: 12/351,056

(22) Filed: Jan. 9, 2009

(65) Prior Publication Data

US 2009/0117831 A1    May 7, 2009

Related U.S. Application Data

(63) Continuation-in-part of application No. 12/080,737, filed on Apr. 4, 2008, now abandoned, and a continuation of application No. 11/092,155, filed on Mar. 29, 2005, now abandoned.

(30) Foreign Application Priority Data

Mar. 30, 2004    (JP)    ............................. 2004-098396

(51) Int. Cl.
    B24B 1/00    (2006.01)
(52) U.S. Cl. ............................................. 451/8; 451/48
(58) Field of Classification Search .................... 451/48, 451/364, 392, 402, 406, 407
    See application file for complete search history.

(56) References Cited

U.S. PATENT DOCUMENTS

| 4,106,242 A | * | 8/1978 | McCandless et al. | ......... 451/394 |
| 5,065,549 A | * | 11/1991 | Speiser et al. | ................. 451/48 |
| 6,149,501 A | * | 11/2000 | Farzin-Nia et al. | ............ 451/48 |

* cited by examiner

Primary Examiner—Maurina Rachuba
(74) Attorney, Agent, or Firm—Townsend & Banta

(57) ABSTRACT

A tapered cutting edge portion and a continuous raised portion from the tapered cutting edge portion are ground in an edge portion of a straight grinding raw material so that an eccentricity is not generated. In a method for grinding a treatment device, one end portion of a tapered grinding raw material is inserted between a grinding surface of a grindstone and a pressing surface of a press block, and finishing surfaces opposite each other while having a predetermined dimension, shape, and angle are ground so that a direction in which abrasive grains of the grindstone run corresponds to a direction of a shaft center. At this point, before the finishing surfaces are ground in the predetermined dimension, shape, and angle which are previously set corresponding to an objective reamer, pre-grinding is performed while a necessary finishing margin with respect to at least one of the surfaces, and then finishing grinding is performed to the other surface.

12 Claims, 15 Drawing Sheets

METHOD OF MANUFACTURING TREATMENT DEVICE AND TREATMENT DEVICE

CROSS-REFERENCE TO A RELATED APPLICATION

This is a continuation-in-part application of U.S. patent application Ser. No. 12/080,737, filed Apr. 4, 2008, now pending, which is a continuation application of U.S. patent application Ser. No. 11/092,155, filed Mar. 29, 2005, now abandoned.

FIELD OF THE INVENTION

The present invention relates to a method for grinding an angular-section tapered bar material which is of an intermediate product when treatment devices such as a dental treatment device, a bone treatment device, and a thrombus depletion device which are tapered from a base portion to a leading end portion. The invention also relates to the tapered treatment device which is produced by adopting the above grinding method.

DESCRIPTION OF THE RELATED ART

Various types of treatment devices, in which the cross section is angular and a region performing the treatment is tapered from the base portion to the leading end, are used in the dental treatment devices or the medical treatment devices. A reamer and a file which are used in the treatment of a root canal can typically be cited as an example of the dental treatment devices. In surgical treatment devices, examples of the treatment devices include the bone treatment device and the thrombus depletion device.

In the treatment device, the thin bar raw material is ground in the tapered shaped to form a working portion having cutting edges or edges according to a treatment object, and an operation portion which is operated by a dentist or a doctor or a shank portion which is grasped by a handpiece is formed adjacent to the working portion. In the case where the working portion is ground, for example the grinding is efficiently performed using a grinding apparatus described in Japanese Patent Application Publication (JP-B) No. 5-87254.

The grinding method and grinding apparatus described in JP-B No. 5-87254 grinds an extremely thin angular cutting edge device which is of the dental treatment device. In JP-B No. 5-87254, a press block is arranged to be opposed to a grinding surface including an outer peripheral surface of a disk-shaped grindstone, the press block can be inclined at a desired angle with respect to the grinding surface, a deadweight of the press block and a weight of a mechanism supporting the press block are caused to act downward by adjusting the deadweight and the weight with a spring, and plural detection devices including dial gauges having contacts for detecting lowering position of the press block and the mechanism supporting the press block are provided.

In the grinding method described in JP-B No. 5-87254, after the inclination angle of a pressing surface of the press block is adjusted with respect to the grinding surface of the grindstone, a grinding raw material is inserted between the pressing surface and the grinding surface, and the grinding is started by causing the press block to come into contact with the grinding raw material to press the grinding raw material against the grindstone while the grindstone is rotated. The press block and the mechanism supporting the press block are lowered with the progress in the grinding to the grinding raw material. When the grinding reaches the predetermined amount of grinding, the detection device for detecting the amount of grinding detects that the grinding reaches the predetermined amount of grinding, and the detection device generates an electrical signal. The grinding is stopped in response to the generated electric signal, the grinding raw material is rotated about the axis of the grinding raw material by 180.degree. or 90.degree., and the grinding of the next process is performed. The grinding is sequentially performed, which completes the grinding of the extremely thin angular cutting device.

In the grinding method described in JP-B No. 5-87254, in the grinding of the grinding raw material, a length region corresponding to the length of the cutting edge portion in the objective extremely thin angular cutting device is ground from a leading end. In this case, because the grinding length for the grinding raw material is shorter than a diameter of the grindstone, it is assumed that the grinding surface is a substantial straight surface. Accordingly, the surfaces ground at four surface of the grinding raw material become flat surfaces, and the cutting edges can be formed at edges in which the surfaces intersecting each other. In the grinding method described in JP-B No. 5-87254, the grinding can be performed at extremely high efficiency and with high accuracy.

In the treatment device, various working portions having sectional sizes and tapers are formed according to functions (the dental treatment device, the bon treatment device, the thrombus depletion device, and the like) and affected regions to which the treatment devices are applied. For example, in the case of a K file for the dental treatment device, the working portions having 28 kinds of numbers are formed in the range of the smallest number of about 0.125 mm to the largest number of about 1.48 mm in the sectional size located 3 mm away from the leading end (the sectional size does not indicate the diameter because the sectional shape is not circular) and the taper of about 2/100. Therefore, the grinding of the treatment device can easily be performed by using the grinding raw material corresponding to the sectional size of the thickest region in the working portions having the various sectional sizes.

However, when the grinding raw material is prepared by causing the diameter of the grinding raw material to correspond to the sectional size of each number, there are generated problems that the number of kinds of the grinding raw materials is remarkably increased and inventory control and production control become complicated. Therefore, it is preferable that the grinding raw material having the diameter which can include several kinds of sectional sizes is used and the plural kinds of treatment devices are produced by grinding the end portion of the grinding raw material. In this case, the objective treatment device is produced by using the grinding raw material having the diameter larger than the sectional size of the thickest region in the working portion.

In the case of using the grinding raw material having the diameter larger than the sectional size of the objective number, it is necessary that the region where the working portion shifts to the shank portion (raised portion) is formed by a smooth ground surface. Therefore, although the length of the raised portion depends on the number, the length of the raised portion set in the range of about 6 mm to about 10 mm, and the raised portion is formed so that the sectional size is smoothly changed from the working portion to the shank portion in the range of the length.

When the cutting edge portion and the raised portion are ground at one time by adopting the technology described in JP-B No. 5-87254, because a grinding length (length of ground surface) is restricted by a position of the raised portion, the amount of grinding (grinding dimension toward a central axis direction from the outer peripheral surface) is increased on the cutting edge side. When the section is ground in the angular shape, there is generated the problem that distances between the central axis of the grinding raw material to the ground surfaces differs from one another, i.e. eccentricity is generated.

This is illustrated in FIGS. 8(a) and 8(b) in which the cutting edge portions and the raised portions of workpiece 75 are ground at one time. In FIG. 8(a), the distance from the central axis 77 to the ground surface 78 is the same as the distance from the central axis 77 to the ground surface 79 on the tip of this material. In other words, little or no eccentricity is generated. However the length between the raised portions $d_a$ is too long. In this case, because it is difficult to twist this workpiece 75, the good treatment device is not provided.

In FIG. 8(b), the distance between the raised portions $d_b$ is shorter than that of FIG. 8(a). However, in this case, an eccentricity is generated on the tip of this material as can be seen in FIG. 8(b). FIG. 9 is a cross-sectional view taken perpendicular to the longitudinal axis of workpiece 75 along line I-I in FIG. 8(b) a length of 5 mm from the tip of the workpiece. It can be seen from FIG. 9 that there is an eccentricity of the ground workpiece at 5 mm from the tip. FIG. 10 is a cross-sectional view taken perpendicular to the longitudinal axis of workpiece 75 along line II-II in FIG. 8(b) at a length of 10 mm from the tip of the workpiece. It can be seen from FIG. 10 that there is an eccentricity of the ground workpiece at 10 mm from the tip.

In the forming of the grinding raw material in which the eccentricity is generated in the cutting edge portion in the objective treatment device, when secondary forming such as twisting and bending is performed, there is generated the problem that the smooth secondary forming is hardly performed. Due to off-balance, there is generated the problem that the treatment device in which the eccentricity is generated in the cutting edge portion is inferior in operability when the doctor operates the treatment device in the treatment. Further, when the treatment device is rotated at high speed during the treatment, there is generated the problem that run-out is created by uneven centrifugal force.

An object of the invention is to provide a grinding method in which an eccentricity is not generated when a tapered cutting edge portion and a continuous raised portion from the tapered cutting edge portion are ground in an edge portion of a straight grinding raw material so that an eccentricity is not generated. Another object of the invention is to provide a tapered treatment device which is manufactured by implementation of the grinding method.

SUMMARY OF THE INVENTION

In order to solve the above problems, a method for grinding a treatment device according to the invention is a method for grinding an angular-section tapered bar for a treatment device, the method for grinding a treatment device in which one end portion of a tapered raw material is inserted between a grinding surface of a grindstone and a press block and finishing surfaces opposite each other while having a predetermined dimension, shape, and angle are ground so that a direction in which abrasive grains of the grindstone run corresponds to an axial direction of the tapered raw material, the method for grinding a treatment device is characterized in that, before the finishing surfaces are ground in the predetermined dimension, shape, and angle previously set corresponding to an objective treatment device, pre-grinding is performed while a necessary finishing margin with respect to at least one of the surfaces, and then finishing grinding is performed to the other surface.

The terminology used in connection with the present invention is described in connection with FIG. 11 which is a cross-sectional view taken along the longitudinal axis of a thin rod or bar-shaped workpiece 40 which is to be ground four times. In a first pre-grinding, a pre-grinding surface 42 is formed. The term "pre-grinding" means "grinding a material in which a finishing margin is left". In other words, the pre-grinding surface 42 is the surface which is left on a first finishing margin 45. In this workpiece 40, a longitudinal axis 47 is shown in long and dashed lines.

After the pre-grinding, the workpiece is rotated 180° and then ground until a second finishing margin 51 is formed.

Thereafter, workpiece 40 is again rotated 180° and the first finishing margin 45 is ground until reaching and exposing a first finishing surface 60 which will become a first cutting edge portion. During this third grinding operation, the raised portion 54 is ground at the same time.

In preferred embodiment, a fourth grinding step then removes at least a portion of the second finishing margin 51, thereby forming and exposing a second finishing surface 48 which will become a second cutting edge. During this fourth grinding operation, the raised portion 57 is ground at the same time.

A tapered treatment device according to the invention which is manufactured by inserting one end portion of a tapered raw material between a grinding surface of a grindstone and a press block and by grinding finishing surfaces opposite each other while having a predetermined dimension, shape, and angle are ground so that a direction in which abrasive grains of the grindstone run corresponds to an axial direction of the tapered raw material, the tapered treatment device has a predetermined tapered shape and grinding traces parallel to the axis of the treatment device in the ground surface by performing pre-grinding while a necessary finishing margin with respect to at least one of the surfaces and by performing finishing grinding to the other surface before the finishing surfaces are ground in the predetermined dimension, shape, and angle previously set corresponding to an objective treatment device.

In the tapered treatment device (hereinafter referred to as treatment device) grinding method according to the invention, when the grinding raw material is ground to form the objective treatment device in the predetermined dimension, shape, and angle, the pre-grinding is performed while the finishing margin is previously left, so that the eccentricity is never generated even if the grinding is performed up to the raised portion. Namely, since the pre-grinding is performed to the grinding raw material at the predetermined angle to leave the finishing margin, the length of the pre-grinding surface can be shortened compared with the predetermined length from the leading end of the grinding raw material to the end portion of the raised portion, and the dimension from the center of the grinding raw material to the pre-grinding surface can be lengthened compared with the predetermined dimension from the center of the grinding raw material to the finishing surface.

After the pre-grinding is performed to one of surfaces in the above-described manner, the other surface is ground. At this point, because the pre-grinding surface comes into contact with the pressing surface of the press block, the other surface is ground while the grinding raw material is deformed toward the press block side. Therefore, when the grinding to the other surface is ended to release the constraint of the press block to the grinding raw material, the raised portion is formed by the ground surface corresponding to the deformed portion.

Then, the grinding raw material is deformed toward the press block side by performing the grinding to the pre-grinding surface, and the raised portion is ground at the same time when the finishing grinding is performed to the pre-grinding surface. When the grinding to the pre-grinding surface is ended to release the constraint of the press block, the raised portion is formed by the ground surface corresponding to the deformed portion.

Accordingly, when the raised portion corresponding to the objective treatment device is ground, the eccentricity is not generated in the working portion. Further, even if the raw material is the extremely thin bar, the bending is not generated by causing the grinding direction (direction in which the abrasive grains run) to correspond to the shaft center, so that the grinding raw material can be ground in the good treatment device.

FIG. 12 illustrates a cross-sectional view taken along the longitudinal axis of a workpiece 63 which has been pre-ground, rotated 180° degrees to form a second finishing surface 65 and then rotated again 180° to remove the finishing margin and expose the first finishing surface 67. Thus, the workpiece 63 shown in FIG. 12 has undergone three grinding operations. FIG. 13 is a cross-sectional view taken perpendicular to the longitudinal axis of workpiece 63 along line I-I in FIG. 12 a length of 5 mm from the tip of the workpiece. It can be seen from FIG. 13 that there is little or no eccentricity of the ground workpiece at 5 mm from the tip. FIG. 14 is a cross-sectional view taken perpendicular to the longitudinal axis of workpiece 63 along line II-II in FIG. 12 at a length of 10 mm from the tip of the workpiece. It can be seen from FIG. 14 that there is little or no eccentricity of the ground workpiece at 10 mm from the tip.

According to the treatment device of the invention, in the cross-section of the working portion of the treatment device, dimensions between the finishing surfaces and the center are substantially equalized, so that the treatment device having good balance and no eccentricity can be formed. Therefore, easy operability can be realized in the treatment device. Further, the uneven centrifugal force is not generated even if the treatment device is rotated at high speed, so that the smooth and stable treatment can be realized.

In a first preferred embodiment there is provided in a method of manufacturing a treatment device using a press block and grindstone to form at one time a cutting edge portion and raised portion from a thin rod or bar-shaped workpiece to form at a leading edge a working portion having extremely thin angular cutting edges and at an opposite end portion a raised portion having a larger diameter than the working portion, the raised portion being formed so that the diameter increases gradually from the working portion, said method involving inserting an end portion of the rod or bar-shaped workpiece into a chuck and an opposite leading end portion of the workpiece between a pressing surface of a press block having an inclination angle of its pressing surface preset with respect to a grinding surface of a disc-shaped grindstone to produce a taper in the working portion of the workpiece, said workpiece being inserted between the press block and grindstone when the grindstone is at rest, and then grinding opposite surfaces of the workpiece to form first and second finishing surfaces in the working portion, while at the same time grinding the raised portions, the improvement comprising the following steps:

(a) calculating the depth of initial pre-grinding of the workpiece on one side thereof at the leading end portion based on set dimensions, taper, grinding length, reference position for the grinding, and length of the working portion;

(b) initiating a pre-grinding beginning at the leading end portion and progressing along the working portion and then the raised portion at the same time, whereby to form a first finishing margin along the working portion;

(c) rotating the workpiece 180°, and then grinding an opposite surface to form a second finishing surface and raised portion at the same time; and (d) rotating the workpiece 180°, and then grinding to remove at least a portion of the first finishing margin along the working portion, whereby to produce a first finishing surface and a ground workpiece substantially free of eccentricity.

In a second preferred embodiment there is provided in the method of the first embodiment in step (c) above, the improvement that the grinding is discontinued before reaching a final second finishing surface, thereby leaving a second finishing margin extending the length of the working portion of the workpiece.

In a third preferred embodiment, there is provided in the method of the second preferred embodiment the improvement that after step (d) above, the workpiece is rotated 180° and then grinding initiated to remove at least a portion of the second finishing margin, whereby to produce a second finishing surface and a ground workpiece substantially free of eccentricity.

In a fourth preferred embodiment there is provided in the method of the first preferred embodiment an improvement in which the treatment device has a spiral groove formed by twisting a ground thin rod or bar-shaped raw material about its axial direction, the first and second finishing surfaces forming cutting edges.

In a fifth embodiment there is provided in the method of the second preferred embodiment an improvement in which the treatment device has a spiral groove formed by twisting a ground thin rod or bar-shaped raw material about its axial direction, the first and second finishing surfaces forming cutting edges.

In a sixth embodiment there is provided in the method of the third embodiment an improvement in which the treatment device has a spiral groove formed by twisting a ground thin rod or bar-shaped raw material about its axial direction, the first and second finishing surfaces forming cutting edges.

In a seventh preferred embodiment there is provided in the method of the first embodiment an improvement in which one end portion of a thin rod or bar-shaped workpiece in steps (b), (c), and (d) are pressed against a grinding surface of a rotating disc-shaped grindstone and grinding is initiated while the workpiece is pressed against the grinding surface of the grindstone with a press block so that a direction traces is similar to an axial direction of the thin rod or bar-shaped raw material.

In an eighth preferred embodiment there is provided in the method of the second preferred embodiment an improvement in which one end portion of a thin rod or bar-shaped workpiece in step (c) is pressed against a grinding surface of a rotating disc-shaped grindstone and grinding is initiated while the workpiece is pressed against the grinding surface of the grindstone with a press block so that a direction traces is similar to an axial direction of the thin rod or bar-shaped raw material.

In a ninth preferred embodiment there is provided in the method of the third preferred embodiment an improvement in which one end portion of a thin rod or bar-shaped workpiece in step (d) is pressed against a grinding surface of a rotating disc-shaped grindstone and grinding is initiated while the workpiece is pressed against the grinding surface of the grindstone with a press block so that a direction traces is similar to an axial direction of the thin rod or bar-shaped raw material.

BRIEF DESCRIPTION OF THE DRAWINGS

FIG. 18 illustrates the location of the finishing margins (by the dashed lines) during the multiple grinding steps employed in grinding away the finishing margins to the depth of the finishing surfaces.

DETAILED DESCRIPTION OF THE PREFERRED EMBODIMENTS

Figure 1:
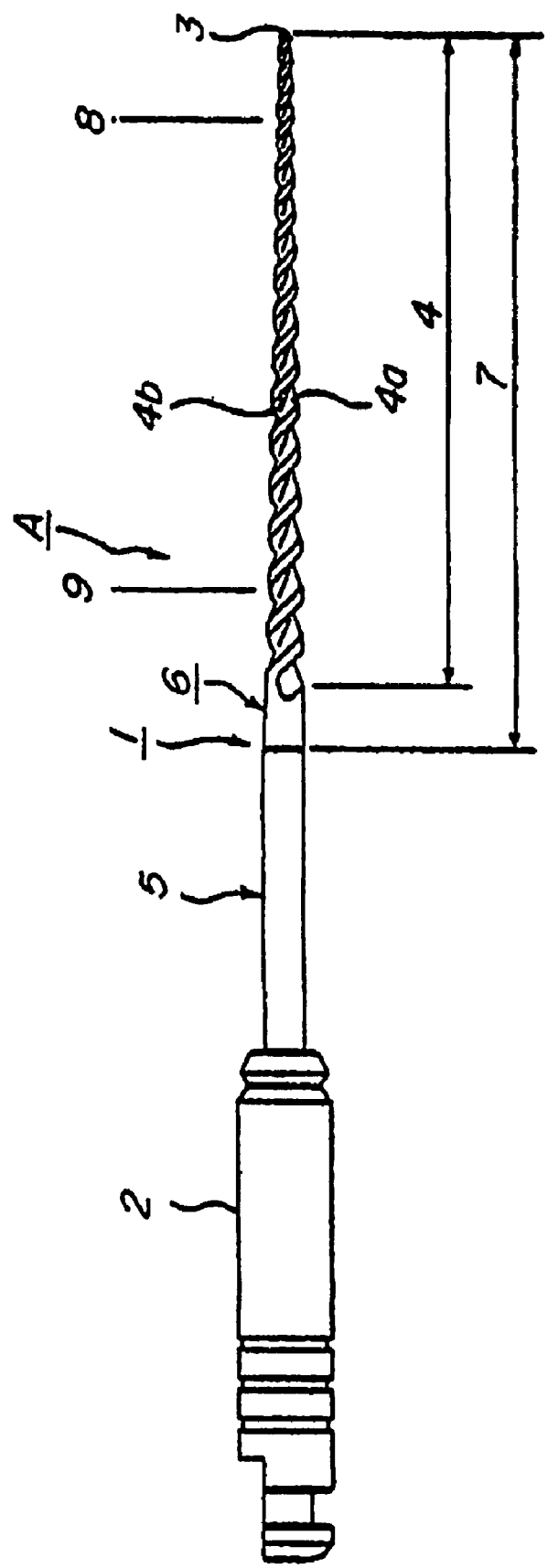
FIG. 1 is a view showing a configuration of a reamer which is of a dental treatment device.

A method for grinding a treatment device and a treatment device according to preferred embodiments of invention will be described below.

The treatment device according to the invention is formed in a tapered shape. A leading-end side of the treatment device has the working portion which has the grinding traces parallel to an axial direction. A sectional shape and dimensions of the working portion, a tapered angle defining a tapered state, an external appearance toward in axial direction, and the like are not particularly limited, and they are appropriately set according to conditions such as a function and number of the objective treatment device.

The treatment device of the invention does not restrict the object devices or types, but the invention can be applied to any tapered treatment device which has a predetermined single taper angle or a complex-angle taper in which the angle is changed depending on a position. Some of this kind of the treatment device has an almost square shaped cross section or a rectangular shaped cross section in its working portion and some of them are twisted to a spiral shape. Example of the treatment device having a square shaped cross section typically includes a reamer and K file. Example of the treatment device having a rectangular shaped cross section typically includes a RT file. Adding to that the treatment device which does not have twisted working portion includes a square brooch. These reamer and files are used for dental treatment. The bone treatment device is used when the bone is treated. The thrombus depletion device is used for depletion of a blood vessel.

In the treatment device of the invention, the working portion including the ground surface having the predetermined angle on the leading-end side, a straight shank portion is formed adjacent to the working portion, the sectional size of the thickest region in the working portion is smaller than the diameter of the shank portion, and a raised portion is formed between the working portion and the shank portion by the grinding.

The grinding raw material is not limited to the particular material, but any material satisfying performances (for example, cutting performance of an affected region, and non-cutting performance to the surrounding) of the objective treatment device can be used as the grinding raw material. For examples in the case where the objective treatment device is a dental root-canal treatment device which cuts a root canal wall, any material which exerts sufficient hardness during the treatment may be used as the grinding raw material.

Examples of the grinding raw material include steel in which the sufficient hardness is obtained by heat treatment, martensitic stainless steel, and Ni—Ti alloys. However, stain tends to be generated at a distribution stage in the steel and martensitic stainless steel, and the secondary forming such as the twisting and the bending is difficult to perform in the Ni—Ti alloys. Therefore, in consideration of good forming characteristics and no generation of the stain, it is preferable that austenitic stainless steel is used as the grinding raw material. However, in the austenitic stainless steel, the hardening is not increased by the heat treatment. It is desirable that the austenitic stainless steel in which work hardening is exhibited by performing cold wire-drawing is used as the grinding raw material.

The sectional shape of the treatment device is not limited to a triangle or a quadrangle. Any treatment device which has the angular sectional shape can be used. Namely, the angular treatment device of the invention includes the treatment device in which two surfaces are ground in parallel or not in parallel in the sectional shape of the grinding raw material.

With reference to the grinding direction for the grinding raw material in the invention, the direction, in which the abrasive grains run, corresponds to the axial direction of the grinding raw material. In order to realize the grinding direction, the outer peripheral of the disk-shaped grindstone is used for the grinding surface, the grinding is performed while the axial direction of the grinding raw material is caused to correspond to the rotating direction of the grindstone, or an endless belt-shaped grindstone is entrained about a pair of rollers and the grinding is performed by rotating the rollers while the rotating direction is caused to correspond to the axial direction of the grinding raw material.

EXAMPLE 1

At first, a typical example of the treatment device according to the invention will be described referring to the drawing. FIG. 1 shows a configuration of a reamer which is of the dental treatment device. A reamer A shown in FIG. 1 is the device which cuts an inner wall surface of a root canal. The reamer A includes a needle portion 1 and a handle 2 attached to an end of the needle portion 1. The reamer A is mainly utilized by attaching the reamer A to a rotating tool such as a handpiece.

In the needle portion 1, a tapered working portion 4 is formed over the given length range from a leading end 3. A rod-shaped shank 5 is formed on the handle 1 side of the needle portion 1. A raised portion 6 is formed between working portion 4 and the shank 5. The taper of the working portion 4 is set at $2/100$ in the K file of the H file pursuant to an international standard (ISO). A reference position in specifying or measuring the sectional size of the working portion 4 is set at a position 8 (first reference position) located 3 mm away from the leading end and a position 9 (second reference position) located 13 mm away from the leading end.

Thus, in the usual dental treatment device, the taper is set at the angle having a gradient of $2/100$. However, the taper is not always set at the above angle. For example, in the flare file, the taper of the working portion 4 is not constant, but the taper is formed so that the gradient is continuously changed in the ranged where the maximum gradient is $5/100$ and the minimum gradient is $2/100$.

The working portion 4 is formed by a spiral groove 4a and a cutting edge 4b along the groove 4a. A length of the working portion 4 is set at about 16 mm from the leading end 3. In the small number range, i.e. in the range of about number 06 to about number 40, a forming length 7 of the raised portion 6 is set at a values not more than 22 mm from the leading end. In the large number range, i.e. in the range of about number 100 to about number 140, the forming length 7 is set at a values not more than 27 mm from the leading end.

Thus, the working portion 4 is a region which actually treats an affected area, and the length of the working portion 4 is strictly set. However, the forming length 7 of the raised portion 6 is not always strictly set, but sometimes a difference is generated to a certain extent due to a relationship between the sectional size at the thickest region in the working portion 4 and the diameter of the grinding raw material.

A dentist manually operates the handle 2, or the handle 2 is grasped by a chuck of the handpiece to be rotated. In Example 1, the handle 2 is formed so as to be grasped by the chuck of the handpiece. The handle 2 is made of synthetic resins or metals such as stainless steel, and the handle 2 is attached to the shank 5 in the needle portion 1. In the attachment of the handle 2 to the needle portion 1, when the handle 2 is made of synthetic resins or metals, the handle 2 having a hole (not shown) is previously formed and the needle portion 1 is inserted into the hole to bond the needle portion 1 to the handle 2 with an anaerobic adhesive.

In the reamer A having the above-described configuration, the dentist inserts the working portion 4 into the root canal of the tooth to be treated while grasping the handpiece to which the handle 2 is attached, and the dentist moves the working portion 4 while the working portion 4 is rotated in the direction of cutting edge 4a, which allows the inner wall surface of the root canal to be cut to perform the forming.

In the treatment devices except for the reamer, the twisted cutting edge 4a is not always formed in the working portion 4, but sometimes the straight cutting edge 4a is formed.

EXAMPLE 2

Figure 2:
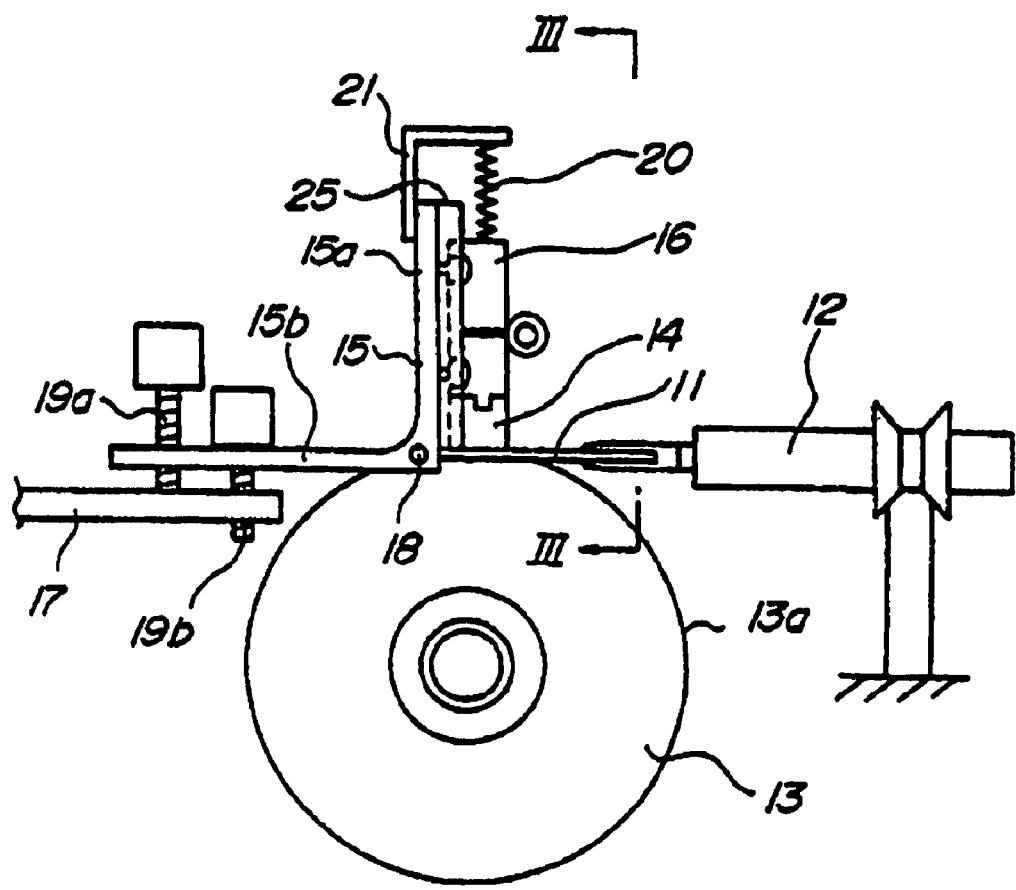
FIG. 2 is a schematic side elevation showing a whole configuration of a grinding apparatus.
Figure 3:
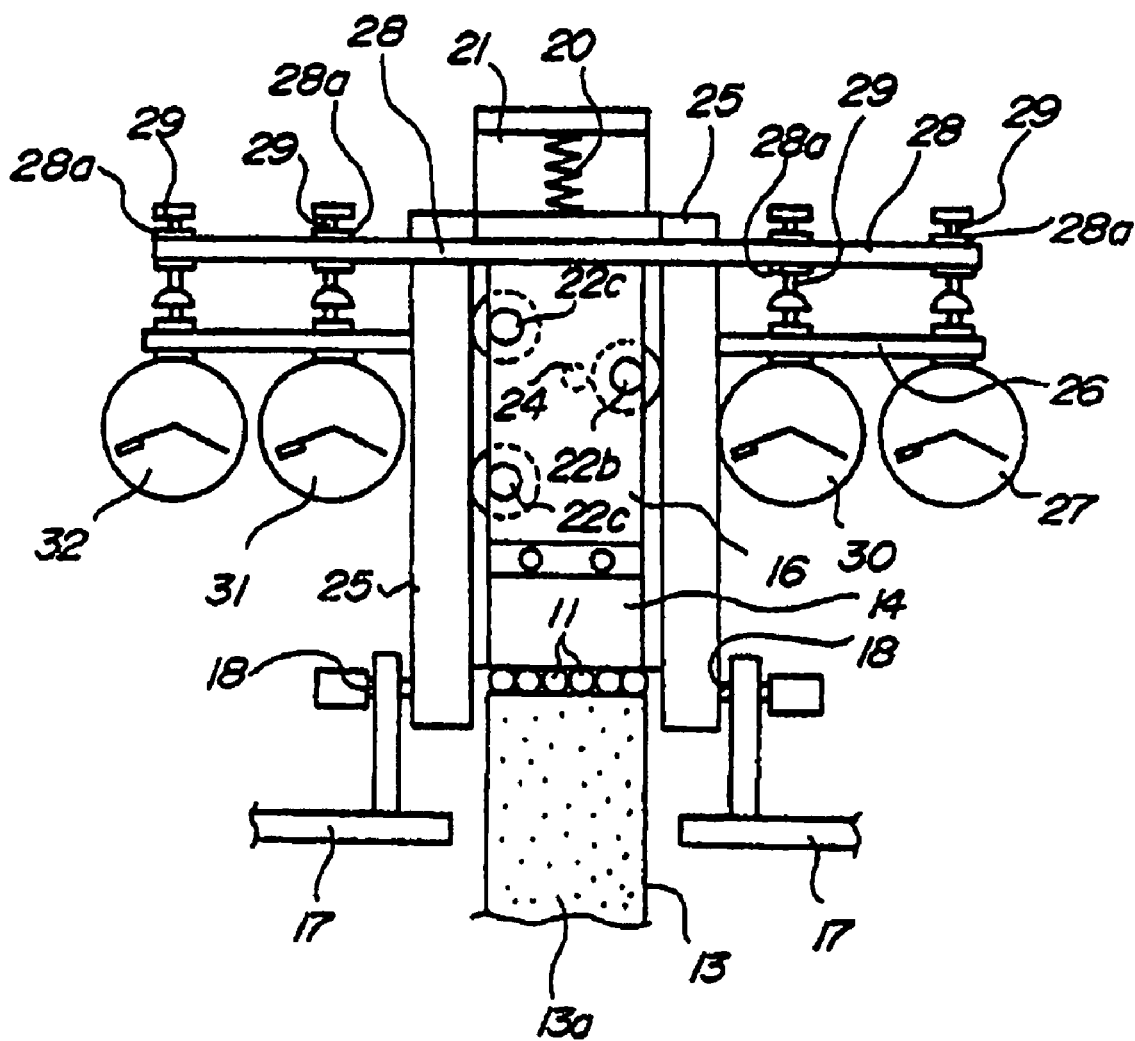
FIG. 3 is a sectional view taken along line III-III of FIG. 2.
Figure 4:
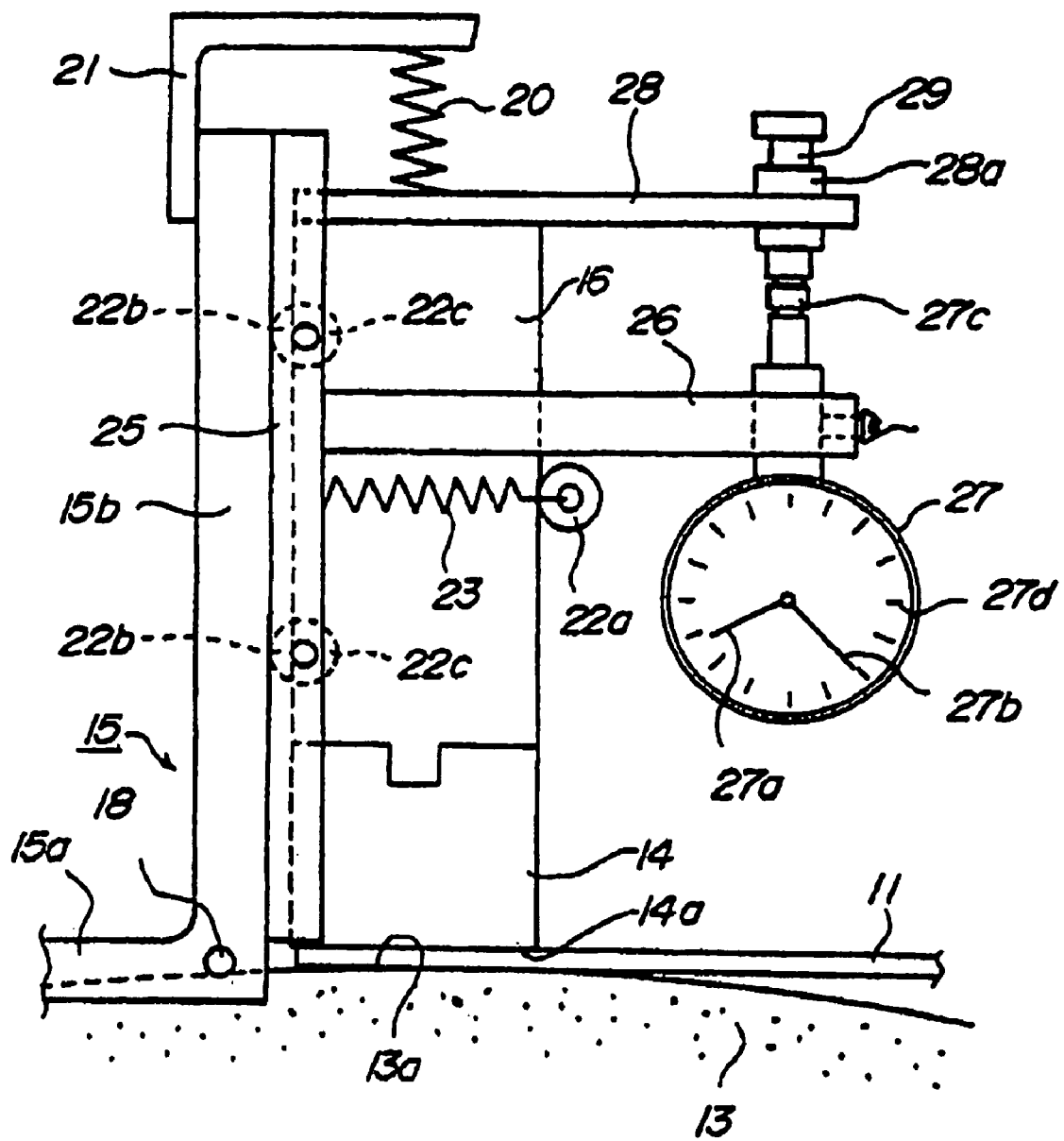
FIG. 4 is a view showing a main part of the grinding apparatus.

Then, a configuration of a grinding apparatus which can perform a grinding method according to the invention will be described referring to the drawings. FIG. 2 is a schematic side elevation showing a whole configuration of the grinding apparatus. FIG. 3 is a sectional view taken along line III-III of FIG. 2. FIG. 4 shows a main part of the grinding apparatus.

In the drawings, a grinding apparatus B includes a chuck 12 which grasps a grinding raw material 11, a grindstone 13 which grinds the grinding raw material 11, and a press block 14 which presses the grinding raw material 11 toward the grindstone 13 side.

The grinding raw material 11 is formed in a thin straight bar with no diameter change. One grinding raw material 11 or the plural grinding raw materials 11 are ground while grasped in the chuck 12. The chuck 12 is arranged opposite a grinding surface 13a which is of a peripheral surface of the grindstone 13. The chuck 12 allows the axial direction of the grinding raw material 11 to correspond to a running direction of the grinding surface 13a while grasping the end portion in a longitudinal direction of the grinding raw material 11.

Because the grindstone 13 has the sufficiently large diameter with respect to a grinding length of the grinding raw material 11, it is assumed that a ground surface formed in the grinding raw material 11 is a flat surface. Namely, the diameter of the grindstone 13 is set at the dimension in which the ground surface is assumed to be the flat surface in grinding the grinding raw material 11.

The press block 14 has both the function of pressing the grinding raw material 11 against the grinding surface 13a of the grindstone 13 with a substantially constant load in grinding the grinding raw material 11 and the function of pressing the grinding raw material 11 against the grinding surface 13a at a predetermined angle.

Therefore, the press block 14 is detachably mounted onto a slide block 16 which is slidably provided along a rise piece 15a of an L-shaped frame 15. The L-shaped frame 15 includes the rise piece 15a and an adjustment piece 15b which is formed in the direction perpendicular to a lower end portion of the rise piece 15a. The L-shaped frame 15 is rotatably attached to shafts 18 provided in support frames 17, and the L-shaped frame 15 is rotated about the shafts 18 associated with the operation of two adjustment screws 19a and 19b provided in the adjustment piece 15b. Therefore, an angle formed between a pressing surface 14a of the press block 14 mounted on the rise piece 15a and the grinding surface 13a can be adjusted.

The slide block 16 is hung from an arm 21 provided in the L-shaped frame 15 through a spring 20. A magnitude of downward force can be adjusted by appropriately setting or adjusting a spring constant of the spring 20. Plural rollers 22a to 22c are rotatably mounted on the slide block 16. The slide block 16 is biased toward the rise piece 15a by a spring 23 attached to the roller 22a, and the rollers 22b and 22c are biased toward a guide 25 provided in the rise piece 15a by a spring 24 attached to the roller 22b, which allows the slide block 16 to slide smoothly in a vertical direction along the rise piece 15.

An arm 26 is protruded from the L-shaped frame 15 or the guide 25 toward the direction of the slide block 16. A detection device 27 is provided on the leading-end side of the arm 26 and at a position where the slide block 16 can be avoided. In the slide block 16, an arm 28 is provided at the position opposite the arm 26. In the arm 28, a nut member 28a is provided at the position opposite the detection device 27. An adjustment screw 29 is screwed in the nut member 28a.

The detection device 27 detects the amount of grinding (grinding depth) to the grinding raw material 11 to generate an electric signal. The detection device 27 measures a lowering amount of the slide block 16, and the detection device 27 can generate the electric signal when the lowering amount reaches the predetermined value. In Example 2, a dial gauge with a contact 27a is used as the detection device 27, and the electric signal can be generated when a pointer 27b comes into contact with the contact 27a.

The adjustment of the detection device 27 will be described. While the press block 14 is elevated, the grinding raw material 11 is inserted between the grinding surface 13a of the grindstone 13 and the pressing surface 14a of the press block 14. In the state of things, the slide block 16 is lowered. When the press block 14 abuts on the grinding raw material 11 to stop the lowering of the slide block 16, the adjustment screw 29 is rotated to cause the adjustment screw 29 to come into contact with a sensor 27c of the detection device 27, and the adjustment screw 27 is further rotated to rotate the pointer 27b while a scale 27d is confirmed so that the pointer corresponds to the predetermined amount of grinding for the grinding raw material 11. When the number of scales between the pointer 27b and the contact 27a corresponds to the predetermined amount of grinding, the rotation of the adjustment screw 29 is stopped, and the adjustment is ended.

The amount of grinding is detected in each grinding to the grinding raw material 11. Accordingly, it is preferable that the detection device has the plural contacts. When the detection device has only one contact, the number of detection devices 27 provided in the grinding apparatus is equal to the number of grinding operations necessary for the grinding raw material 11. For example, in the grinding apparatus B shown in FIG. 3, four detection devices 27, 30, 31, and 32 are provided, and each of the detection devices 27, 30, 31, and 32 can detect the amount of grinding in one of four grinding times to generate the electric signal.

In the grinding apparatus B, the L-shaped frame 15 is inclined by operating the adjustment screws 19a and 19b, which adjusts the angle formed between the pressing surface 14a of the press block 14 and the grinding surface 13a of the grindstone 13. Then, as described above, generation points of the electric signals (the lowering amounts of the slide block 16 and the press block 14) are set in each of the detection devices 27 and 30 to 32 by rotating the adjustment screws 29 corresponding to the detection devices 27 and 30 to 32. In the state of things, when the grinding is performed to the grinding raw material 11 by rotating the grindstone 13, the slide block 16 is lowered as the amount of grinding is increased, and the pointer 27b of the detection device 27 (30 to 32) is brought close to the contact 27a. When the pointer 27b comes into contact with the contact 27a, the electric signal is generated. The rotation of the grindstone 13 is stopped in response to the electric signal, and the grinding to the grinding raw material 11 is stopped.

When a first grinding operation in which a first surface is ground is completed, the grinding raw material 11 currently grasped by the chuck 12 is rotated by 180°, or 90° by operating the chuck 12, and a second grinding operation is performed to a second surface of the grinding raw material 11. In the grinding raw material 11, the ground surface whose grinding traces correspond to the axial direction is formed by the repetition of the grinding.

EXAMPLE 3

Figure 5:
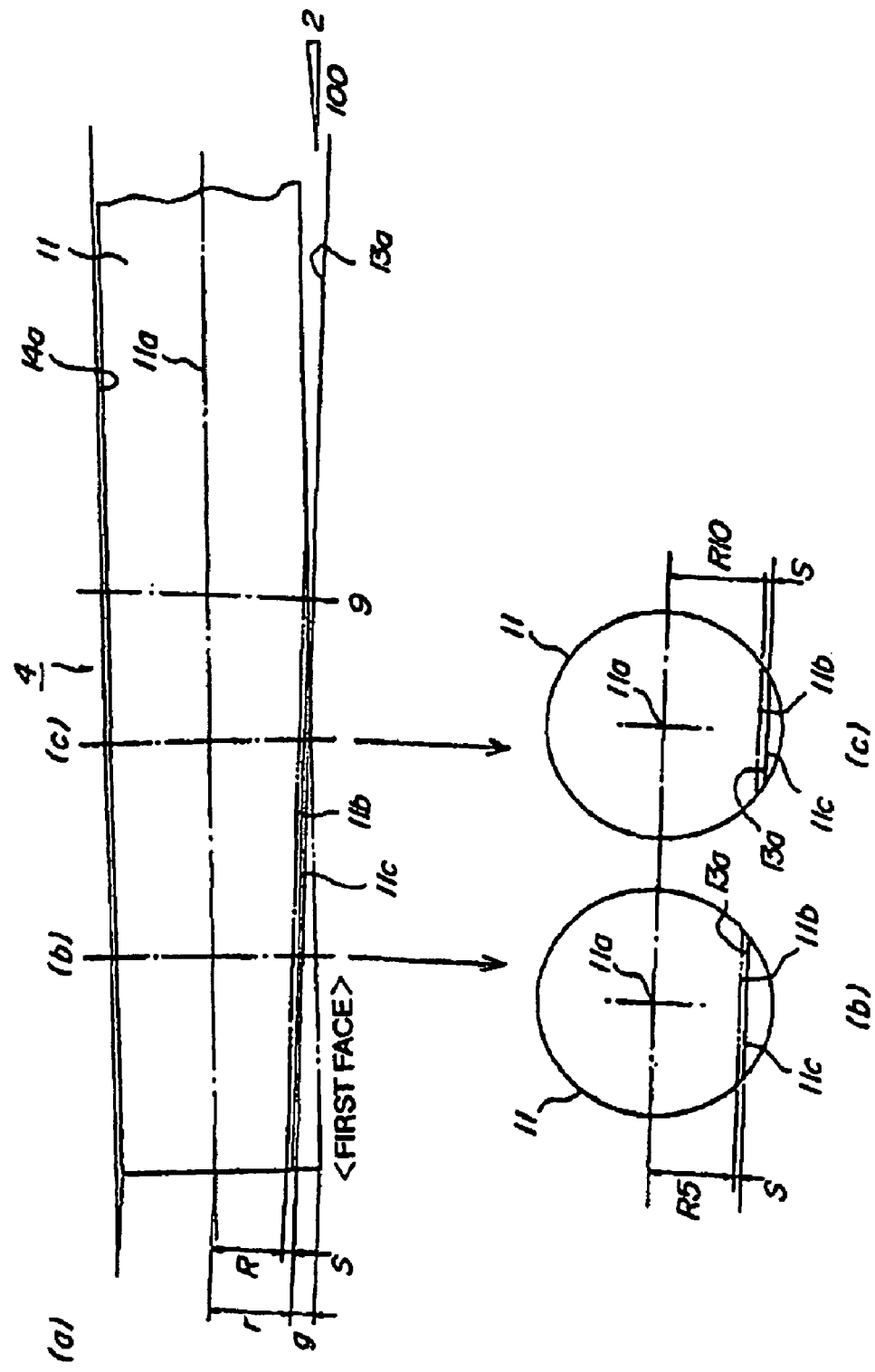
FIG. 5 is a view showing pre-grinding to a grinding raw material 11.
Figure 6:
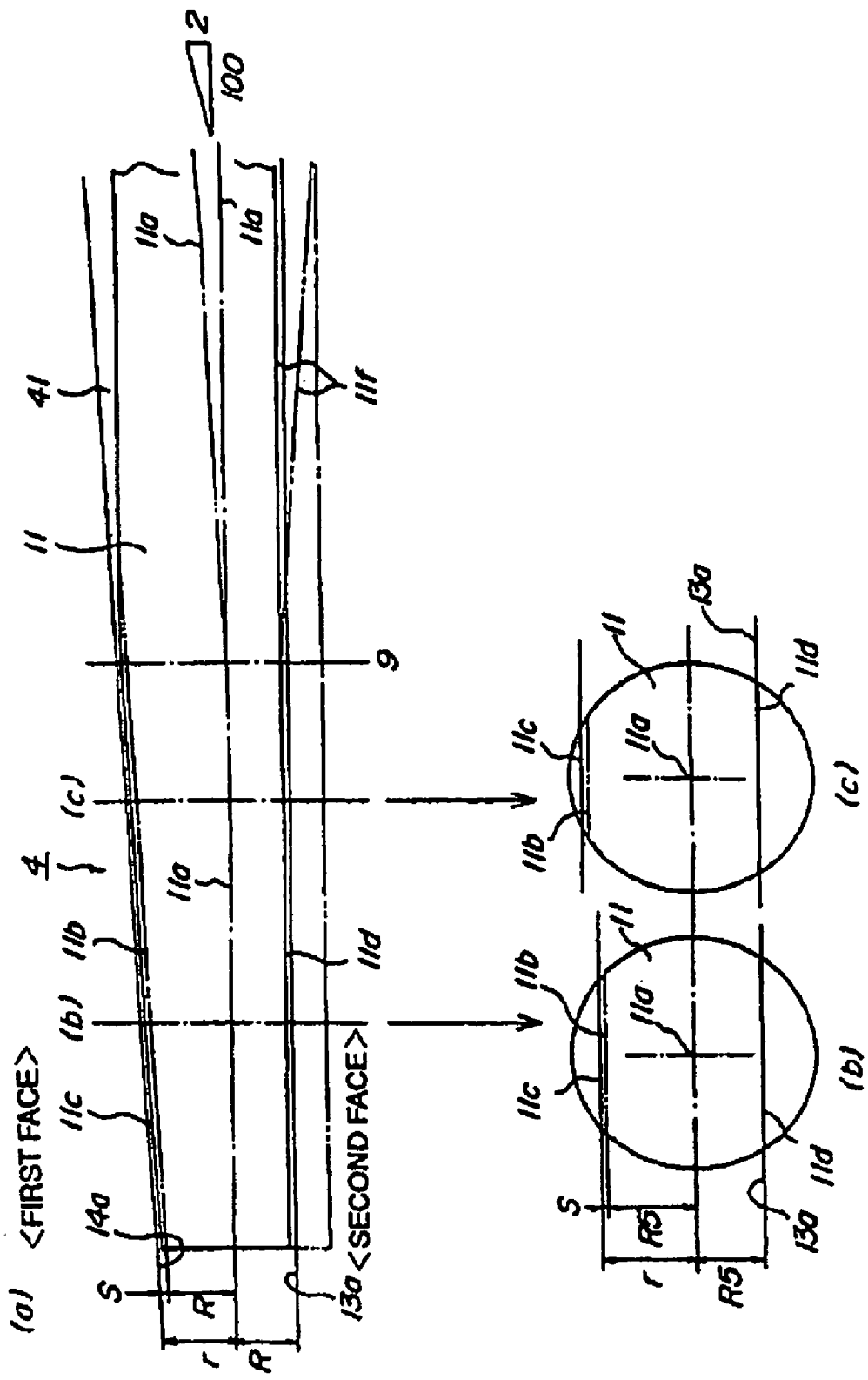
FIG. 6 is a view for explaining a state in which the grinding is performed to a surface opposite a pre-grinding surface to which the pre-grinding is already performed.
Figure 7:
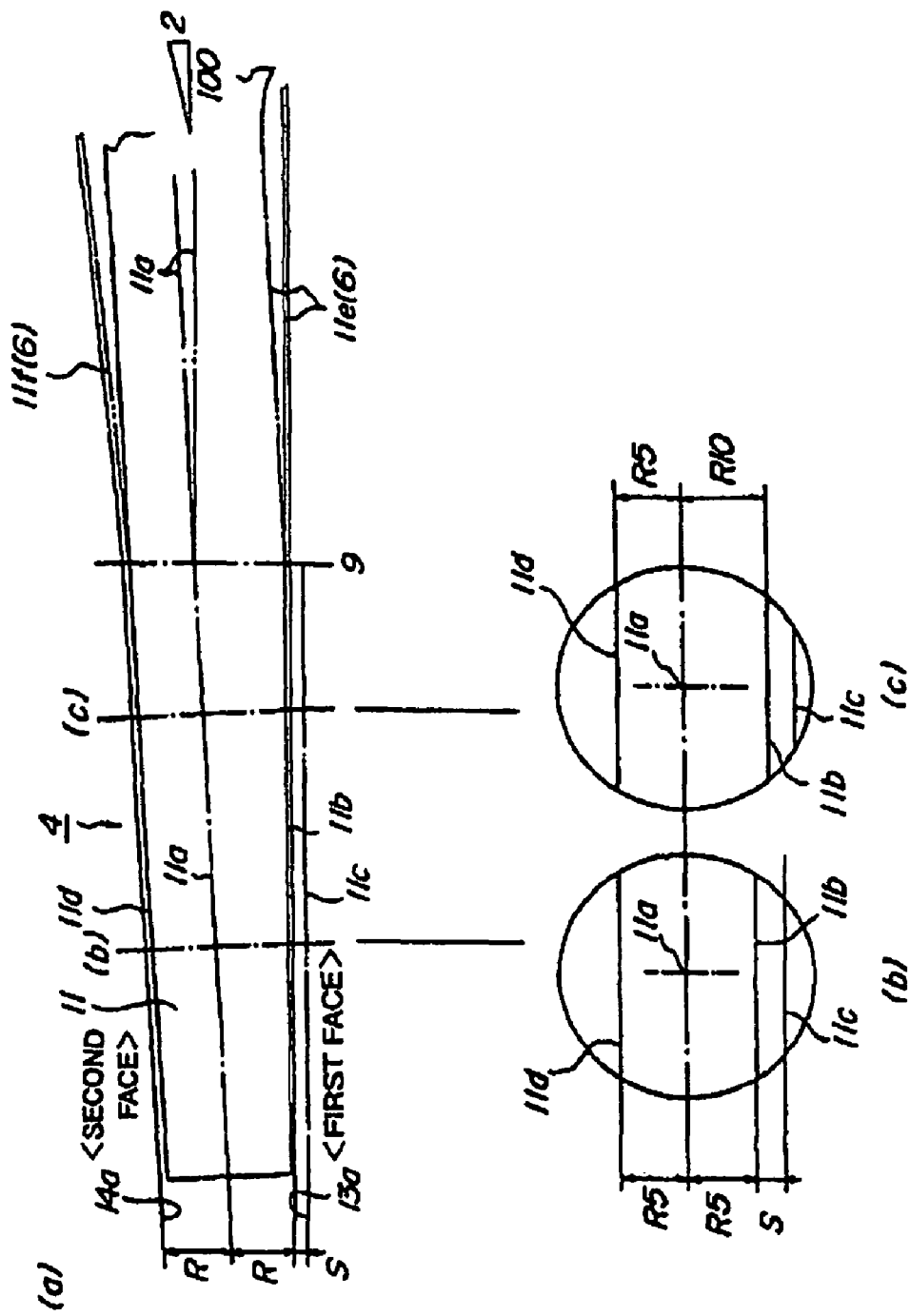
FIG. 7 is a view for explaining a state in which the grinding is performed to the pre-grinding surface.
Figure 8A:
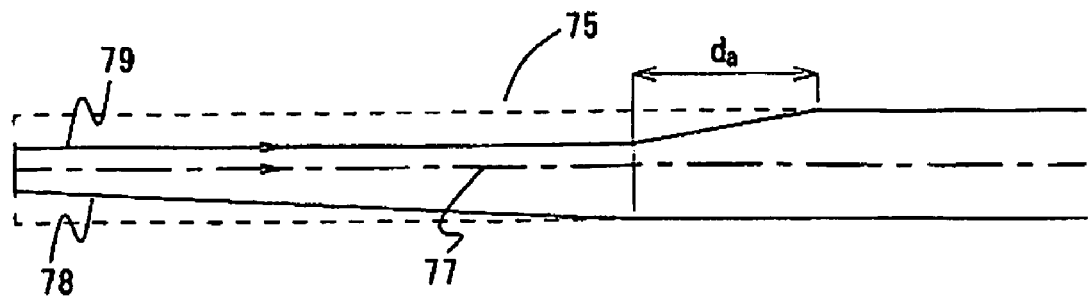
FIG. 8(a) is a cross sectional view taken along a longitudinal axis of a workpiece, illustrating the lack of eccentricity in the ground working portion, and large difference in the position of the raised portion.
Figure 8B:
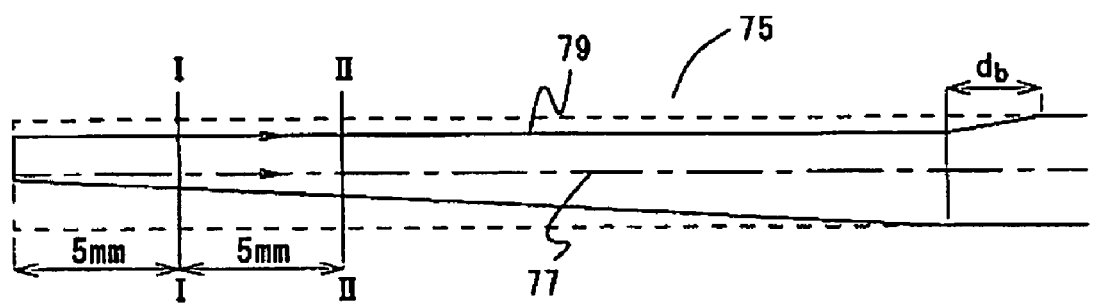
FIG. 8(b) is a cross sectional view taken along a longitudinal axis of a workpiece, illustrating the eccentricities generated at the sectional lines I-I (5 mm from the leading end) and II-II (10 mm from the leading end) in the ground surfaces.
Figure 9:
FIG. 9 is a cross-sectional view taken at 5 mm from a tip along line I-I of the workpiece of FIG. 8(b) which has been ground only once on each of its opposite sides, illustrating the generated eccentricities of the ground surfaces.
Figure 10:
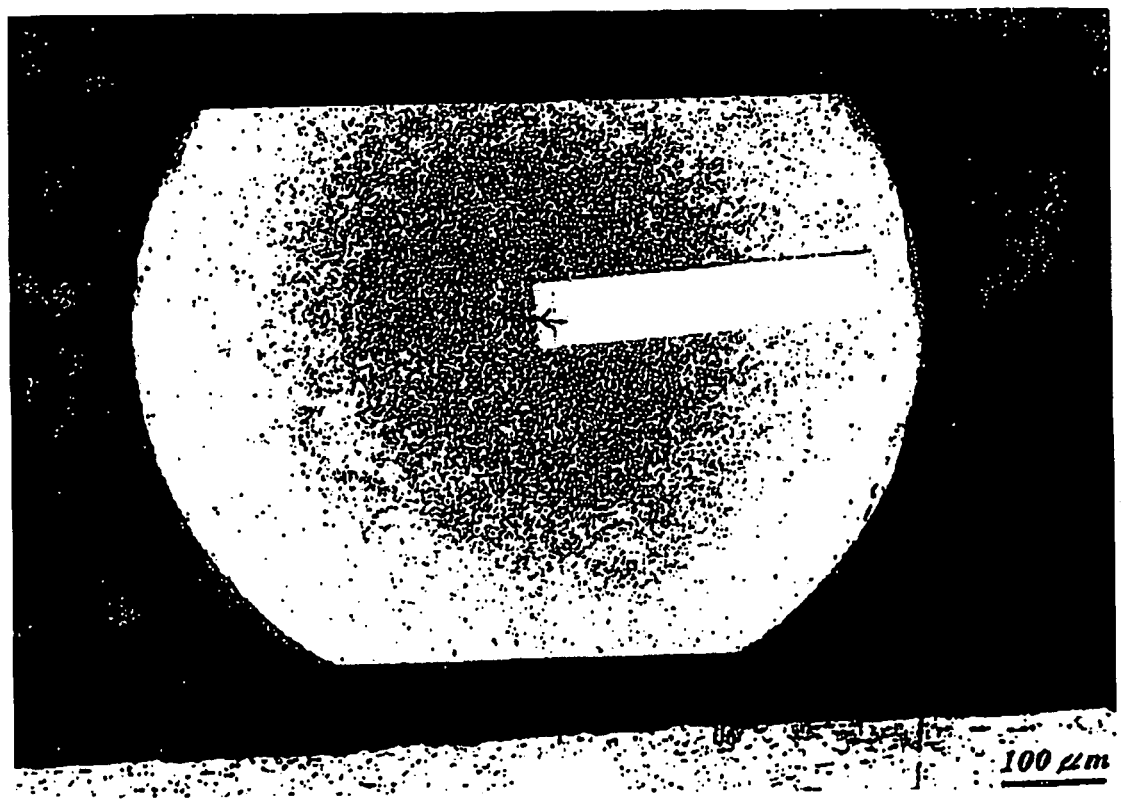
FIG. 10 is a cross-sectional view taken at 10 mm from a tip along line II-II of the workpiece of FIG. 8(b) which have been ground by the prior art method only once on each of its opposite sides, illustrating the eccentricities of the ground surfaces.
Figure 11:
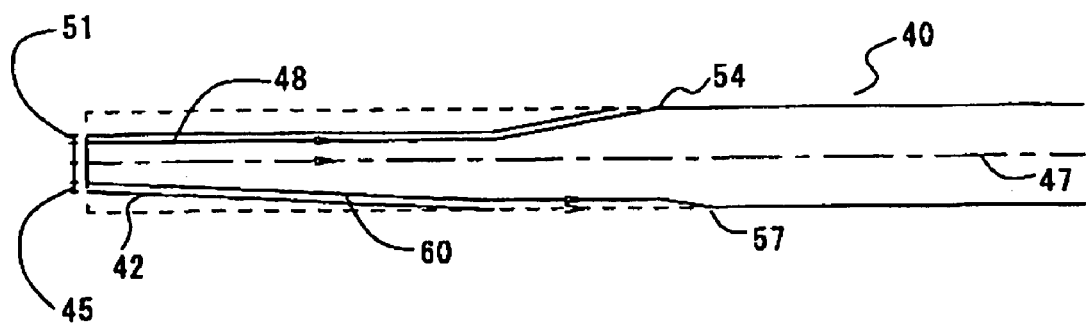
FIG. 11 is a cross-sectional view taken along the longitudinal axis of a workpiece ground according to a preferred embodiment of the present invention, illustrating the results of four grinding operations in which there are formed first and second finishing margins, a pre-grinding surface, first and second finishing surfaces, and raised portions formed at the same time as the working portion.
Figure 12:
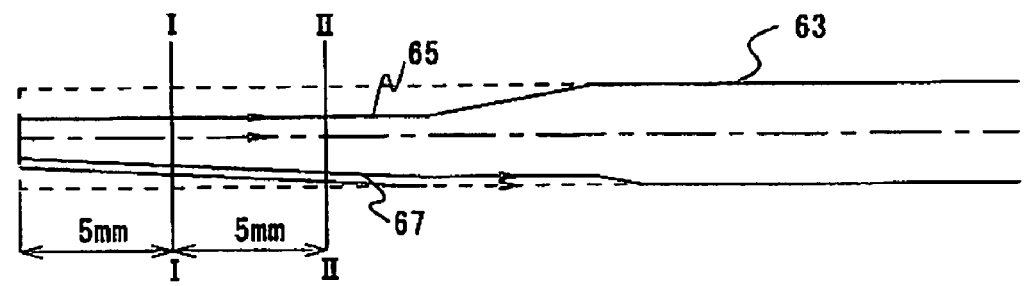
FIG. 12 is a cross-sectional view taken along a longitudinal axis of a workpiece in which the cutting edge portion and raised portion are ground at the same time by the method of the present invention, illustrating particularly that the position of the raised portion is nearer than that shown in FIGS. 8(a) and (b), and also illustrating that little or no eccentricity is generated at the tip of the working portion.
Figure 13:
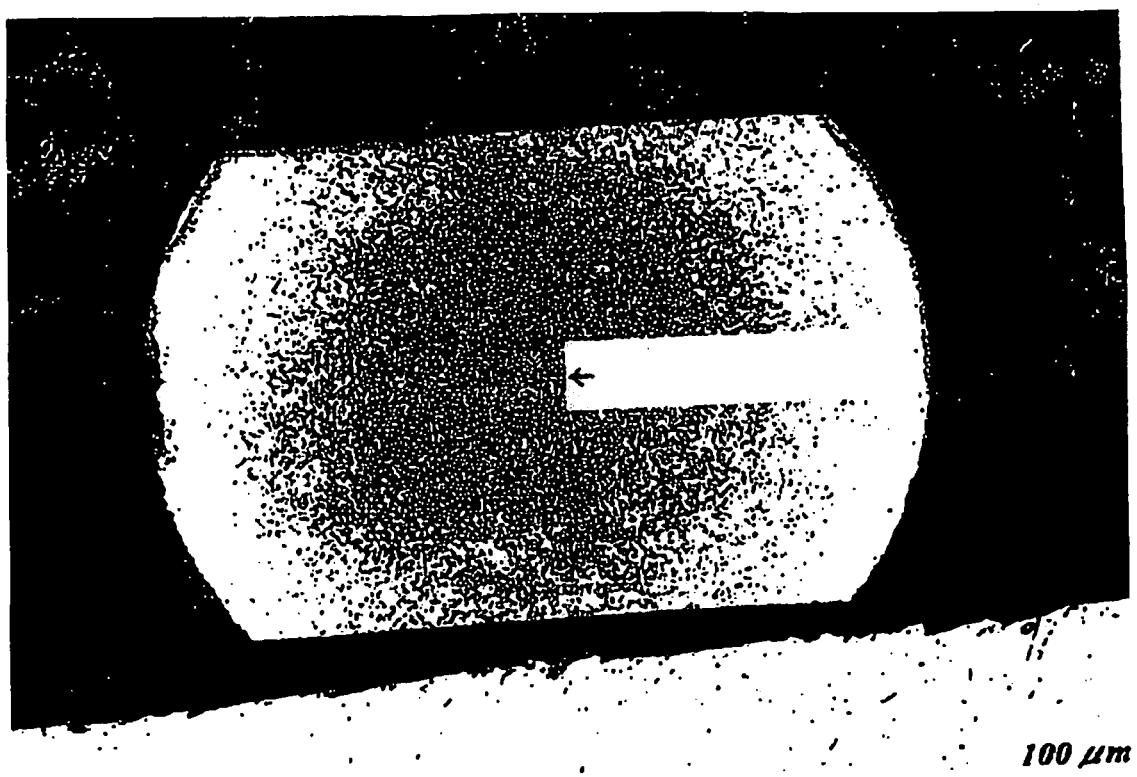
FIG. 13 is a cross-sectional view taken perpendicular to the longitudinal axis of the workpiece of FIG. 12 along line I-I at 5 mm from the tip which has been ground by the method of the present invention involving grinding the workpiece three times to form a pre-grinding surface before grinding a second finishing surface, followed by grinding the first finishing margin to form the first finishing surface, illustrating that there is little or no eccentricity in the ground workpiece 5 mm from its tip.
Figure 14:
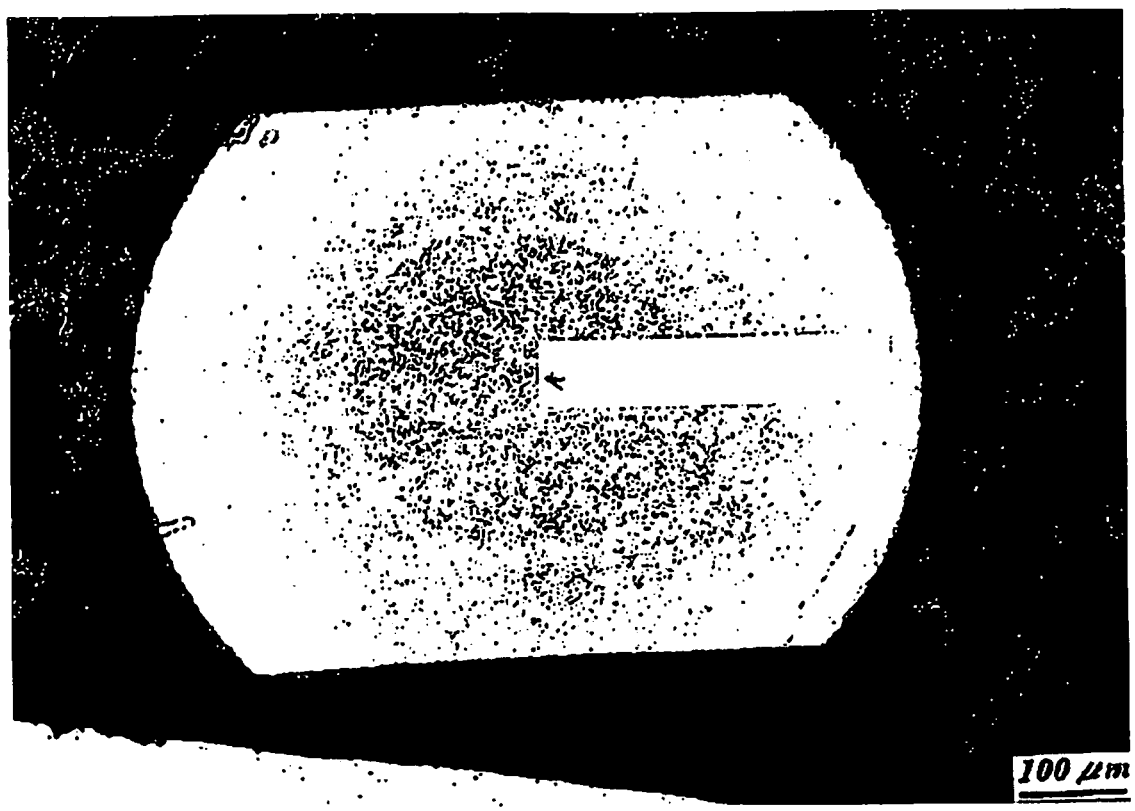
FIG. 14 is a cross-sectional view taken perpendicular to the longitudinal axis of the workpiece of FIG. 12 along line II-II 10 mm from the tip which has been ground by the method of the present invention involving grinding the workpiece three times to form a pre-grinding surface before grinding a second finishing surface, followed by grinding the first finishing margin to form the first finishing surface, and illustrating that there is little or no eccentricity in the ground workpiece 10 mm from its tip.

Then, the grinding method according to Example 3 of the invention will be described referring to drawings. FIG. 5 is a view showing pre-grinding to the grinding raw material 11. FIG. 6 is a view for explaining the state in which the pre-grinding is performed to a pre-grinding surface to which the pre-grinding is already performed. FIG. 7 is a view for explaining the state in which the grinding is performed to the pre-grinding surface.

The grinding raw material 11 shown in FIGS. 5 to 7 is the raw material for producing the reamer A shown in FIG. 1. In the grinding raw material 11, cold wire drawing is performed to a wire rod made of austenitic stainless steel at a predetermined diameter-reduction ratio to realize work hardening, and a texture elongated in a fibrous shape is realized to exert strength against bending. When the grinding raw material 11 is ground to form the cutting edge, grinding performance can be secured in the cutting edge. Even if the bending force is applied during the treatment of the affected area, the grinding raw material 11 can stand up to the bending force.

The working portion 4 of the reamer A is formed with the taper of 2/100. Therefore, in the press block 14, the gradient of the pressing surface 14a is set so as to have the taper of 2/100 with respect to the grinding surface 13a of the grindstone 13. Namely, the L-shaped frame 15 is rotated about the shaft 18 by operating the adjustment screws 19a and 19b, which adjusts the tilt angle of the pressing surface 14a with respect to the grinding surface 13a to set the taper at 2/100.

After the taper of the pressing surface 14a of the press block 14 is set with respect to the grinding surface 13a of the grindstone 13, one end portion of the grinding raw material 11 is grasped by the chuck 12 and the other end portion is inserted between the grinding surface 13a and the pressing surface 14a. The end portion of grinding raw material 11 is placed on the grinding surface 13a without rotating the grindstone 13, and the pressing surface 14a is caused to come into contact with the peripheral surface of the grinding raw material 11. Thus, in the grinding raw material 11, a shaft center 11a is placed in parallel with the pressing surface 14a and has the taper of 2/100 with respect to the grinding surface 13a by causing the peripheral surface of the grinding raw material 11 to come into contact with the pressing surface 14a.

At this point, the leading-end portion of the grinding raw material 11 is in contact with the grinding surface 13a, and which becomes a reference of the amount of grinding in measuring the amount of grinding. Accordingly, the contacts 27a of the detection devices 27 and 30 to 32 are adjusted in this state. For example, when the detection device 27 corresponds to the pre-grinding which is of the first grinding operation, the dimension between the contact 27a and the pointer 27b is caused to correspond to the predetermined amount of grinding at the end portion of the grinding raw material 11 in the pre-grinding by operating the adjustment screw 29 provided opposite the detection device 27.

In Example 3, the position (second reference point 9) located 13 mm away from the leading end of the grinding raw material 11 is set at the reference position for the grinding so that the grinding length becomes about 13 mm in the pre-grinding. A finishing margin corresponding to the difference between the forming length 7 of the raised portion 6 (not more than the range of about 22 mm to about 27 mm from the leading end of the grinding raw material 11) and the grinding length in the pre-grinding is defined by setting the grinding end portion at 13 mm in the pre-grinding.

As shown in FIG. 5, the amount of grinding in the pre-grinding is detected as the amount of grinding at the leading end portion of the grinding raw material 11. However, it is difficult to inspect the dimension of the leading end portion, so that the reference position for the dimensional measurement of the grinding raw material 11 is set at the position located predetermined distance away from the leading end (For example, 5 mm or 10 mm, the position (b) or position (c) in FIG. 5A), the dimension at each position is set with respect to the dimension at the position located 13 mm away from the end portion of the grinding raw material 11 which is of the grinding end portion. The amount of grinding at the leading end is calculated from the set dimension and taper, the value of the calculation result is specified as the amount of pre-grinding in the pre-grinding.

Figure 15:
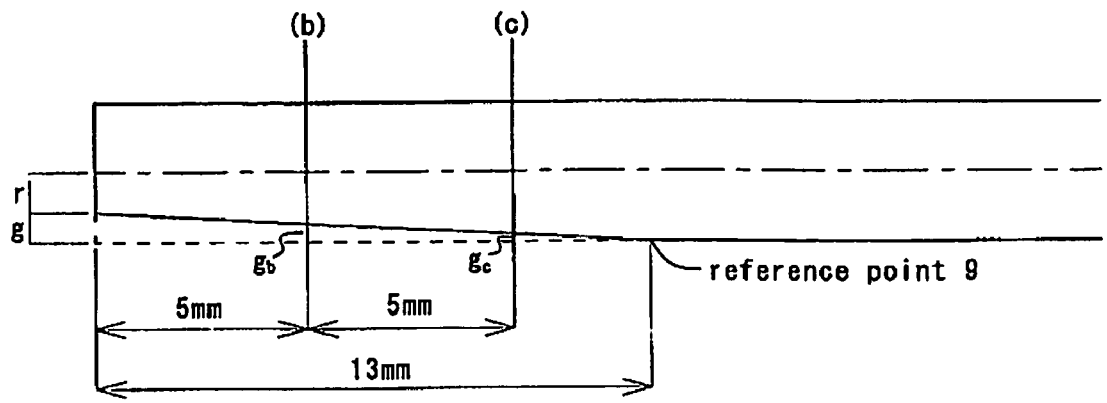
FIG. 15 is a cross-sectional view taken along the longitudinal axis of a workpiece illustrating the shape of the workpiece after grinding only one surface of the workpiece.
Figure 16:
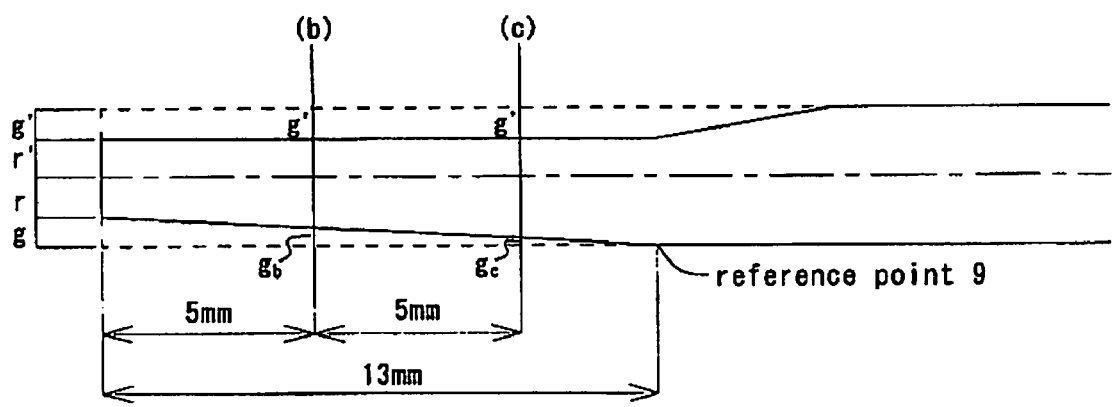
FIG. 16 is a cross-sectional view taken along the longitudinal axis of a workpiece illustrating the shape of the workpiece after the workpiece has been preground on one side, and then ground on an opposite surface.
Figure 17:
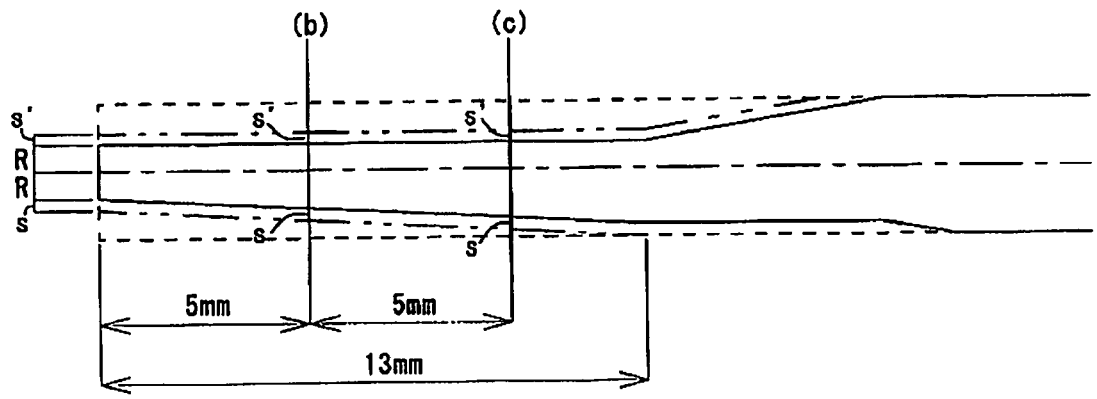
FIG. 17 is a cross-sectional view taken along the longitudinal axis of a workpiece, illustrating the shape of the workpiece after the workpiece has been preground, so as to leave a finishing margin, rotated 180°, and then ground on an opposite surface, so as to leave a second finishing margin, which is then removed. The removed finishing margins are shown by the dot-dot-dash lines.

The method of calculating the amount of grinding is explained below with respect to FIGS. 15, 16 and 17. These FIGS. 15, 16 and 17 illustrate cross sectional views of a workpiece which has undergone grinding according to the process of the present invention. In particular, FIG. 15 illustrates a workpiece having one side ground to a depth of g at the leading end, with the grinding extending along a working portion to reference point 9. The length of the ground portion is illustrated as being 13 mm, and sectional lines (b) and (c) are 5 mm and 10 mm from the leading edge, respectively.

FIG. 16 is a cross sectional view of a workpiece in which both opposite surfaces have been ground in the working portion, and the grinding continued to the raised portion.

FIG. 17 is a cross sectional view of a workpiece 11 illustrating the shape of the workpiece, a location of a removed finishing margin formed on one side, and a location of a removed finishing margin formed on an opposite side, said removed finishing margins being illustrated by the dot-dot-dash lines.

When the amount of grinding reaches g in FIG. 15, g' in FIG. 16, and s and s' in FIG. 17, respectively, the detection devices 27, 30, 31 and 32, as shown in FIGS. 2-4, detects same, and generates and transmits an electric signal (i.e., a command), directing the halt of the rotation of the grindstone.

In this Example 3, the position (second reference point 9) located 13 mm away from the leading end of the grinding raw material 11 is set as the reference position for the grinding, so that the length of grinding length in the pre-grinding step is about 13 mm, as can be seen in FIGS. 15 and 16. It can also be seen that the amount of grinding at the reference point 9 in FIGS. 15 and 16 is 0 mm.

The amount of grinding (g, g', s and s') is calculated as follows: The amount of taper is predetermined, in this Example 3 being 2/100. The amount of pre-grinding g, gb and gc, as illustrated in FIG. 15, can be calculated as follows:

$$g = 13 \times \frac{2}{100} \text{(at the leading end portion)}$$

$$g_b = g \times \frac{8}{13} \text{(at the section } (b)\text{)}$$

$$g_c = g \times \frac{3}{13} \text{(at the section } (c)\text{)}$$

With regards to the second finishing margin, as illustrated in FIG. 16, the amount of g' is arbitrary if r' (as shown in FIG. 16) is greater than R (as shown in FIG. 17). As illustrated in FIGS. 16 and 17, the amount of grinding required to remove the finishing margin (designated as s and s') can be calculated as follows:

$$s = r - R$$

$$s' = r' - R$$

As a result of the calculation corresponding to the objective reamer A, assuming that the dimension between the shaft center 11a and a first finishing surface 11b at the end portion of the grinding raw material 11 is set to R and the finishing margin is set to s, a dimension r (pre-grinding surface dimension) between the shaft center 11a and a pre-grinding surface 11c becomes R+s. Accordingly, a dimension g in which R+s is subtracted from a radius of the grinding raw material 11 becomes the amount of pre-grinding.

Figure 18:
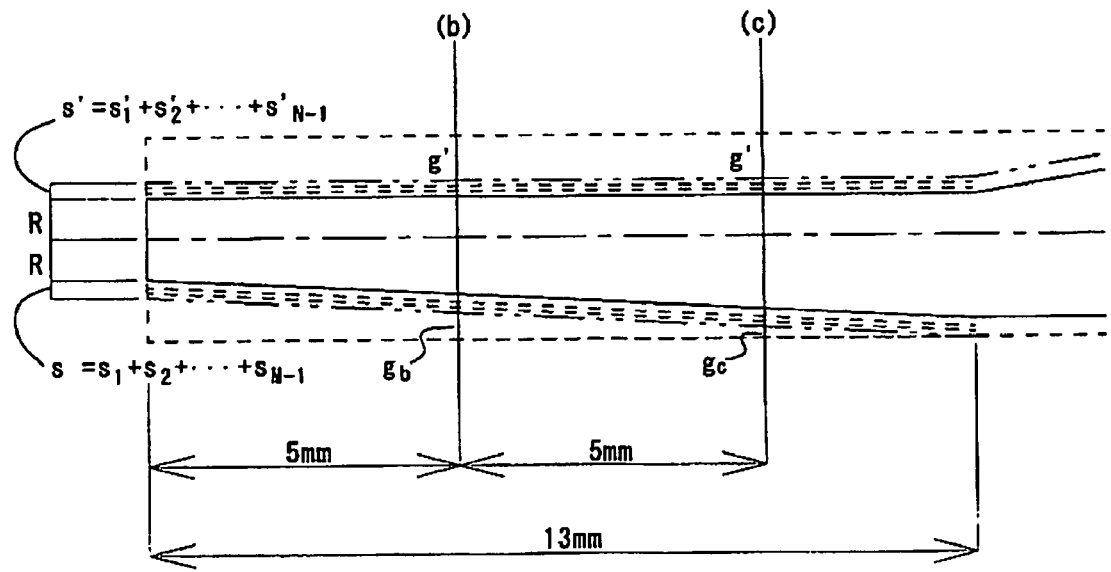
FIG. 18 is a cross-sectional view taken along the longitudinal axis of a workpiece, in which the working surfaces have been ground, together with the raised portion at the same time, and finishing margins have been formed on the workpiece, and then ground away in multiple grinding steps, until reaching the finishing surfaces. In particular.

In a preferred embodiment, more than three grinding steps are carried out. The amount of grinding in each of these steps is not crucial; the important variable being that all of the finishing margins are removed in the multiple grinding steps down to the finishing surface. For example, if dividing the finishing margin into M−1, the finishing margin "s" is considered to be "$s = s_1 + s_2 + \ldots + s_{M-1}$" ($s_1, s_2, \ldots, s_{M-1}$). Then on one side of a workpiece, the number of grinding steps becomes M (pre-grinding step and M−1 steps). If the number of grinding steps on the other side of a workpiece is N, the total steps becomes M+N, as shown in FIG. 18.

The taper is generated on a workpiece by pre-grinding. When the workpiece is ground after the pre-grinding, the surface after grinding becomes parallel to the surface before grinding. In other words, the amount of grinding at the leading edge is same as the amount of grinding at position (b) and (c), as shown in FIG. 18, after the second grinding step.

Therefore, in the detection device 27, the dimension between the contact 27a and the initial pointer 27b is set so as to correspond to the amount of pre-grinding g. In other detection devices, for example, the amount of grinding for grinding a second finishing surface 11d opposite the pre-grinding surface 11c becomes the dimension (the amount of second finishing grinding) in which the finishing surface dimension R is subtracted from the radius of the grinding raw material 11, i.e. g+r−R as shown in FIG. 6.

In a further preferred embodiment, the plurality of grinding steps carried out to remove the first finishing margin and the second finishing margin may be performed in alternating steps. For example, the method of the present invention may be performed by first partially grinding the first finishing margin, rotating the workpiece 180°, partially grinding the second finishing margin, rotating the workpiece 180°, again partially grinding the first finishing margin, rotating the workpiece 180°, and repeating this procedure until both the first and second finishing margins are entirely removed.

The detection device 30 is specified as detection device which detects the amount of grinding (the amount of second finishing grinding) of the second finishing surface 11d, and the position of the contact is adjusted while the grinding is not performed to the grinding raw material 11. Then, the dimension between the contact and the pointer becomes 2 g+r−R in which the amount of pre-grinding g is added to the amount of second finishing grinding g+r−R. Similarly the detection device 31 is specified as detection device which detects the amount of first finishing grinding of the first finishing surface 11b, and the position of the contact is adjusted while the grinding is not performed to the grinding raw material 11. Then, the dimension between the contact and the pointer becomes 2 g+2 r−2 R in which the amount of pre-grinding g and the finishing margin s are added to the amount of second finishing grinding g+r−R.

Thus, the taper of the pressing surface 14a of the press block 14 is set with respect to the grinding surface 13a of the grindstone 13, the contact points of the detection devices 27, 30, and 31 are set, and the pre-grinding is performed. When the grindstone 13 is rotated, the pre-grinding is performed to the grinding raw material 11. As shown in FIG. 5A, the pre-grinding is started from the end portion of the grinding raw material 11 while the shaft center 11a of the grinding raw material 11 is held in parallel with the pressing surface 14a. When the amount of grinding reaches the amount of pre-grinding g, the detection device 27 generates the electric signal, and the rotation of the grindstone 13 is stopped based on the electric signal. Accordingly, the pre-grinding is ended for the grinding raw material 11.

FIG. 5B is a sectional view at the position located 5 mm away from the leading end of the grinding raw material 11. In this case, R5 indicates the dimension between the shaft center 11a of the grinding raw material 11 and the first finishing surface 11b, and R5 becomes the dimension in which an increment according to the taper of 2/100 is added to the dimension R between the shaft center 11a and the first finishing surface 11b at the end portion. Similarly, FIG. 5C is a sectional view at the position located 10 mm away from the leading end, and RIO becomes the dimension in which the increment according to the taper of 2/100 is added to the dimension R.

When the pre-grinding is ended, the press block 14 is elevated, the chuck 12 is returned to rotate the chuck 12 by 180.degree., and then a second grinding operation is performed. In the second grinding operation, the opposite surface to the pre-grinding surface 11b which is of the un-grinding surface of the grinding raw material 11 is faced toward the grinding surface 13a of the grindstone 13 and inserted between the grinding surface 13a and the pressing surface 14a. Then, as shown in FIG. 6, the press block 14 is lowered to cause the pressing surface 14a to abut on the pre-grinding surface 11c of the grinding raw material 11. At this point, a gap 41 is formed between the pressing surface 14a and the grinding raw material 11, and the shaft center 11a of the grinding raw material 11 is arranged in parallel with the grinding surface 13a.

In the state of things, when the grindstone 13 is rotated, in the grinding raw material 11, the contact region with the grinding surface 13a of the grindstone 13 is ground from the leading-end portion. The length of the contact region is sufficiently longer than the length of the pre-grinding surface 11c (contact length with the pressing surface 14a). Therefore, the grinding raw material 11 is bent toward the press block 14 side by force acting on the grinding raw material 11 (the shaft center 11a shown by an alternate long and short dashed line is bent as shown by a thin chain double-dashed line), and the peripheral surface of the grinding raw material 11 abuts on the pressing surface 14a to be supported.

Accordingly, in the surface opposite the pre-grinding surface 11c, the second finishing surface 11d is ground while the taper of 2/100 is maintained. However, the continuous surface from the second finishing surface 11d is ground while bent toward the pressing surface 14a side. Therefore, an extended line of a grinding surface 11f reaches the outer periphery of the grinding raw material 11.

When the detection device 30 detects that the amount of grinding reaches the amount of second finishing grinding, the electric signal is generated, and the rotation of the grindstone 13 is stopped. When the press block 14 is elevated, the grinding raw material 11 is released from constraint of the press block 14, which allows the grinding raw material 11 to return to the straight shape, and the second raise surface 11f (raised portion 6) is formed by the grinding surface 11f. Namely, in the grinding raw material 11, the shaft center 11a shown by the thin chain double-dashed line is returned to the state shown by the alternate long and short dashed line, which allows the grinding surface 11f shown by a solid line is displaced as shown by a thick chain double-dashed line to form the second raise surface 11f (raised portion 6).

After the second finishing surface 11d and the second raise surface 11f of the second surface are ground in the above-described manner, the chuck 12 is returned to rotate the chuck 12 by 180°. Then, the pre-grinding surface 11c of the first surface is faces toward the grinding surface 13a of the grindstone 13, and the press block 14 is lowered to perform the third grinding operation. Namely, as shown in FIG. 7, the pressing surface 14a of the press block 14 is caused to abut on the second finishing surface 1d of the grinding raw material 11. At this point, in the grinding raw material 11, part of the second finishing surface 11d (leading end of the grinding raw material 11) and part of the second raise surface 11f (contact portion between the second raise surface 11f and the outer periphery of the grinding raw material 11) abut on the pressing surface 14a.

When the load of the press block 14 applied to the grinding raw material 11 while the pressing surface 14a of the press block 14 abuts on the second finishing surface 11a of the grinding raw material 11, in the grinding raw material 11, the shaft center 11a shown by the alternate long and short dashed line is bent like the shaft center 11a shown by the thin chain double-dashed line according to the abutment of the second raise surface 11f on the pressing surface 14a. Therefore the continuous outer-peripheral surface from the pre-grinding surface comes into contact with the grinding surface 13a of the grindstone 13.

In the state of things, when the grindstone 13 is rotated, the finishing grinding to the pre-grinding surface 11c and the grinding outer peripheral surface of the grinding raw material 11 are performed, and the continuous first raise surface 11e from the first finishing surface 11b is formed while the first finishing surface 11b is formed in the pre-grinding surface 11c. The press block 14 is lowered with the progress on the grinding. When the detection device 31 detects that the amount of grinding to the grinding raw material 11 reaches the amount of first finishing grinding, the rotation of the grindstone 13 is stopped by the electric signal from the contact.

When the press block 14 is elevated, the grinding raw material 11 is released from the constraint of the press block 14, which allows the grinding raw material 11 to return to the straight shape (the shaft center 11a shown by the thin chain double-dashed line returns to the shaft center 11a shown by the alternate long and short dashed line). Therefore, the first finishing surface 11b and the first raise surface 11e (raised portion 6) shown by the thick chain double-dashed line are formed.

In the first finishing surface 11b formed in the above-described manner, the dimension from the shaft center 11a of the grinding raw material 11 reaches the finishing surface dimension R. Namely, since both the dimension from the shaft center 11a to the first finishing surface 11b and the dimension from the shaft center 11a to the second finishing surface 11d become R, there is no eccentricity. In the embodiment, the first surface is formed by the first and third grinding operations and the second surface is formed by the second and fourth grinding operations. However, it is possible that the finishing margin is also left in the second grinding operation and the finishing margin is removed in the fourth grinding operation.

As described above, the object product of the invention can be applied to the devices such as the dental treatment device, the bone treatment device, and the thrombus depletion device.

In the embodiments mentioned above, grinding operations to the first surface and the second surface, which are in relation in front and back, are explained. But in a case of a cross section of the treatment device is a square, the third surface and the forth surface which respectively correspond to the first surface and the second surface could be ground by the same manner of grinding operation. They could be ground in a manner that the first surface is ground, the third face, which is the side face for the first surface, is ground, the second face is ground, then the forth surface is ground, which is the side face for the second surface and the grinding turn of the each surfaces is varied. Also in the first grinding operation is the pre-grinding in the above embodiment, but the second grinding operation could be the pre-grinding. The number of times of pre-grinding operation is not limited to once and the pre-grinding operation could be plural times.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

What is claimed is:

1. In a method of manufacturing a treatment device using a press block and grindstone to form at one time a cutting edge portion and raised portion from a thin rod or bar-shaped workpiece to form at a leading edge a working portion having extremely thin angular cutting edges and at an opposite end portion a raised portion having a larger diameter than the working portion, the raised portion being formed so that the diameter increases gradually from the working portion, said method involving inserting an end portion of the rod or bar-shaped workpiece into a chuck and an opposite leading end portion of the workpiece between a pressing surface of a press block having an inclination angle of its pressing surface preset with respect to a grinding surface of a disc-shaped grindstone to produce a taper in the working portion of the workpiece, said workpiece being inserted between the press block and grindstone when the grindstone is at rest, and then grinding opposite surfaces of the workpiece to form first and second finishing surfaces in the working portion, while at the same time grinding the raised portions, the improvement comprising the following steps:
   (a) calculating the depth of initial pre-grinding of the workpiece on one side thereof at the leading end portion based on set dimensions, taper, grinding length, reference position for the grinding, length of the working portion;
   (b) initiating a pre-grinding beginning at the leading end portion and progressing along the working portion and then the raised portion at the same time, whereby to form a first finishing margin along the working portion;
   (c) rotating the workpiece 180°, and then grinding an opposite surface to form a second finishing surface and raised portion at the same time; and
   (d) rotating the workpiece 180°, and then grinding to remove at least a portion of the first finishing margin along the working portion, whereby to produce a first finishing surface and a ground workpiece substantially free of eccentricity.

2. The method of claim 1, wherein in step (c) above, the grinding is discontinued before reaching a second finishing surface, thereby leaving a second finishing margin extending the length of the working portion of the workpiece.

3. The method of claim 2, wherein after step (d) above, the workpiece is rotated 180° and then ground to remove at least a portion of the second finishing margin, whereby to produce a second finishing surface and a ground workpiece substantially free of eccentricity.

4. A method for manufacturing a treatment device according to claim 1, wherein the treatment device has a spiral groove formed by twisting a ground thin rod or bar-shaped raw material about its axial direction, the first and second finishing surfaces forming cutting edges.

5. A method for manufacturing a treatment device according to claim 2, wherein the treatment device has a spiral groove formed by twisting a ground thin rod or bar-shaped raw material about its axial direction, the first and second finishing surfaces forming cutting edges.

6. The method for manufacturing a treatment device according to claim 3, wherein the treatment device has a spiral groove formed by twisting a ground thin rod or bar-shaped raw material about its axial direction, the first and second finishing surfaces forming cutting edges.

7. The method of claim 1, wherein one end portion of a thin rod or bar-shaped workpiece in steps (b), (c), and (d) above is pressed against a grinding surface of a rotating disc-shaped grindstone and grinding is initiated while the workpiece is pressed against the grinding surface of the grindstone with a press block so that a direction traces is similar to an axial direction of the thin rod or bar-shaped raw material.

8. The method of claim 2, wherein one end portion of a thin rod or bar-shaped workpiece in step (c) above is pressed against a grinding surface of a rotating disc-shaped grindstone and grinding is initiated while the workpiece is pressed against the grinding surface of the grindstone with a press block so that a direction traces is similar to an axial direction of the thin rod or bar-shaped raw material.

9. The method of claim 3, wherein one end portion of a thin rod or bar-shaped workpiece in step (d) above is pressed against a grinding surface of a rotating disc-shaped grindstone and grinding is initiated while the workpiece is pressed against the grinding surface of the grindstone with a press block so that a direction traces is similar to an axial direction of the thin rod or bar-shaped raw material.

10. The method of claim 1, wherein, in step (d), the grinding to remove at least a portion of the first finishing margin is carried out in a plurality of separate grinding steps.

11. The method of claim 3, wherein the grinding to remove at least a portion of the second finishing margin is carried out in a plurality of separate grinding steps.

12. The method of claim 1 wherein the plurality of grinding steps of the first finishing margin and the plurality of the grinding steps of the second finishing margin are performed in alternating steps.

\* \* \* \* \*